US00PP15050P2

(12) United States Plant Patent
van Dijk

(10) Patent No.: US PP15,050 P2
(45) Date of Patent: Jul. 27, 2004

(54) ANTHURIUM ANDREANUM PLANT NAMED 'ANTHEFAQYR'

(50) Latin Name: *Anthurium andreanum*
Varietal Denomination: Anthefaqyr

(75) Inventor: Jan van Dijk, Bleiswijk (NL)

(73) Assignee: Anthura B.V. (NL)

( * ) Notice: Subject to any disclaimer, the term of this patent is extended or adjusted under 35 U.S.C. 154(b) by 0 days.

(21) Appl. No.: 10/612,049

(22) Filed: Jul. 3, 2003

(51) Int. Cl.[7] ..... A01H 5/00
(52) U.S. Cl. ..... Plt./366
(58) Field of Search ..... Plt./366, 365

*Primary Examiner*—Kent Bell
(74) *Attorney, Agent, or Firm*—Foley & Lardner

(57) ABSTRACT

A new and distinct cultivar of Anthurium plant named 'Anthefaqyr', as described and illustrated and particular characterized by the combined features of the plant flowers early and fully and can be sold at different stages, from a mini-type of 35 cm in height to a larger plant that is 70 cm in height; the scape is long and erect, resulting in inflorescences held well above the foliage; the plant habit is full due to shoot formation; the leaves are dark green, compact and durable with light green primary veins; the flowers are durable and white in color, slowly turning green as they mature; and the amount of inflorescences is large in relation to the amount of leaf blades resulting in excellent leaf to inflorescence ratio.

4 Drawing Sheets

Latin name of the Genus and species of the plant claimed: *Anthurium andreanum* L.
Variety denomination: Anthefaqyr.

BACKGROUND OF THE INVENTION

'Anthefaqyr' is a new and distinct cultivar of Anthurium, botanically known as *Anthurium andreanum* L. The new cultivar is a white, naturally occurring, single plant mutation of Anthurium plant named 'Pink Champion' (U.S. Plant Pat. No. 12,115), and was obtained from a production clone of the cultivar 'Pink Champion' in Bleiswijk, The Netherlands, in 1999.

The female or seed parent of 'Pink Champion' was a pink-red-colored proprietary *Anthurium andreanum* hybrid having selection number 93-372-02 (unpatented). The male or pollen parent was *Anthurium andreanum* 'Sweet Heart Pink' (unpatented).

The white, single plant mutation was discovered and selected as a flowering plant within a planting of the production clone of *Anthurium andreanum* 'Pink Champion' by the inventor Jan van Dijk. The plant was asexually reproduced by tissue culture in Bleiswijk, The Netherlands, at a temperature of 21 degrees Celsius.

BRIEF DESCRIPTION OF THE INVENTION

The following traits have been repeatedly observed and in combination distinguish 'Anthefaqyr' as a new and distinct cultivar:

1. The plant flowers early and fully and can be sold at different stages, from a mini-type plant of 35 cm in height to a larger plant that is 70 cm in height;
2. The scape is long and erect, resulting in inflorescences held well above the foliage;
3. The plant habit is full due to shoot formation;
4. The leaves are dark green, compact and durable with light green primary veins;

5. The inflorescences are durable and white in color, slowly turning green as they mature.
6. The amount of inflorescences is large in relation to the amount of leaf blades resulting in excellent leaf to inflorescence ratio.

In comparison to the parental cultivar 'Pink Champion', 'Anthefaqyr' is white (RHS 156D; both surfaces), and 'Pink Champion' is pink (RHS 52B; upper surface and RHS 51B; lower surface).

'Anthefaqyr' has not been observed under all possible environmental conditions. The phenotype of the new cultivar may vary significantly with variations in environment such as temperature, light intensity, and daylength, without any change in the genotype.

BRIEF DESCRIPTION OF THE DRAWINGS

The accompanying photographic drawings, taken in Bleiswijk, The Netherlands, show typical 'Anthefaqyr' plants. The photographic drawings portray colors as true as is reasonably possible with colored reproductions of this type.

FIG. 1 is a side-view of 'Anthefaqyr' showing the inflorescences held well above the leaf canopy.

FIG. 2 is a close-up of an 'Anthefaqyr' inflorescence showing the spathe and spadix.

FIG. 3 is a close-up of 'Anthefaqyr' inflorescences at three different stages of development: from young on the left to old on the right. The youngest inflorescence has an unripe spadix (pistils are not visible yet). The inflorescence in the middle has a ripe spadix without any pollen. The spathe of the old inflorescence on the right becomes green. Between the left and the right inflorescences is a difference in age of approximately 15 to 20 weeks.

FIG. 4 is a close-up of the top of a young (left) and old leaf blade (right) showing the difference between old and young leaf blades. It shows that the young leaf blades are lighter green than the old leaf blades.

DETAILED BOTANICAL DESCRIPTION

The following observations, measurements and values describe 60 week old plants as grown in 17 cm containers, in Bleiswijk, The Netherlands, under greenhouse conditions, which closely approximate those generally used in horticultural practice.

Color references are made to The Royal Horticultural Society (R.H.S.) Colour Chart, except where general color terms of ordinary significance are used. The color references are approximate, as color depends to a degree on horticultural practices such as light level and degree of fertilization, among others. The color values were determined between 11:00 a.m. and 3:00 p.m. on Apr. 15, 2003, under 5000 lux natural light in a glasshouse in Bleiswijk, The Netherlands.

The phenotype may vary significantly when grown under different conditions of temperature, light or other determining factors, without a change in genotype of the plant.

Classification:

*Botanical.*—*Anthurium andreanum* L. 'Anthefaqyr'.

*Commercial denomination.*—*Anthurium andreanum* L., cv White Champion.

Parentage: Single plant mutation selected within a planting of the production clone of Anthurium 'Pink Champion'.

Propagation: Asexual propagation by means of tissue culture and all propagation that flowered have been true to type in plant and flower characteristics. The instant plant's characteristics are firmly fixed and retained through successive generations of asexual reproduction. The new plant reproduces true to type through successive generations of asexual reproduction.

Plant description: Approximately 55–60 weeks following division, 'Anthefaqyr' will reach a mature size of approximately 35 cm to 70 cm in height and approximately 35 cm to 55 cm in width in a 17-cm container. The plant is compact and freely branching.

Leaves:

*Form.*—The leaf blade is elliptical-cordate with an acuminate tip and a cordate base, with an entire margin. The leaf blade angle to the petiole is between 110 and 140 degrees. Leaf blades enlarge as the plant ages and some axillary shoots with small leaf blades are also produced. A wide range in leaf blade length and width is found on each plant. The minimum leaf blade length is approximately 3 cm and the maximum leaf blade length is approximately 18 cm. The minimum leaf blade width is approximately 1.5 cm and the maximum leaf blade width is approximately 10 cm. Mature leaf blades are cupped.

*Texture.*—Leaf blades are leathery and thick.

*Veins.*—The mid-vein and primary veins (the veins, which radiate out from the juncture of the petiole and leaf) protrude at the underside of the leaf blade. The light-green color of the veins at the upper surface (RHS 144A) and the lower surface (RHS 144B) of the mid-vein and primary veins (approximately 6 to 8) contrast with the more dark-green color of the upper surface of the leaf blade.

*Leaf blade-color.*—The leaf blade upper surface is RHS 137A; the leaf blade lower surface is light-green (RHS 146B).

*Lobes.*—A leaf blade has two lobes extending past the petiole. The distance from petiole/leaf juncture to the highest point on the lobes of mature leaf blades (width 10 cm, length 18 cm) ranges approximately from 4 to 5 cm.

*Petiole.*—Green (RHS 146B); the cross section of the petiole is round and the diameter is approximately 2 to 5 mm, length is 10–15 cm. The color of the cataphylls surrounding the petioles is RHS 175A.

Spathe:

*Buds.*—The spathe is tightly rolled around the spadix and extrudes from the peduncle sheath. The spathe is fully open at approximately the same time that the peduncle fully elongates.

*Size.*—The completely developed spathe of a 40-cm tall plant is approximately 7 cm to 8 cm long and approximately 5 cm to 8 cm wide.

*Color.*—When just fully open, the upper and lower surface is white RHS156D. After approximately 10 weeks, the spathe is fully open and the surface starts to turn green beginning at the spadix and the lobes of the spathe. The white color slightly turns green. After another 10 weeks, the spathe is completely green (RHS 145A). The primary veins of the spathe are slightly darker green.

*Arrangement.*—The spathe angle to the scape is between 100 and 120 degrees. The spathe stands on a straight wiry peduncle approximately 6 cm to 15 cmabove the foliage. The scape cross-section is round and the diameter approximately 3 mm to 6 mm, depending on the age of the plant. The scape is erect and ranges from approximately 15 to 45 cm depending on the age of the plant. The scape is light green in color (RHS 144A).

*Shape.*—The spathe is cordate (heart-shaped) with a mucronate tip and a cordate base; with an entire margin. A just fully opened spathe is cup-shaped. The lobes of the spathe stay upward. As the flower ages, the tip bends upwards slightly.

Flowering time: One small-untreated tissue culture plant of approximately 2 cm in height will flower, depending on season, after approximately 16 to 17 months when approximately 3 to 4 inflorescences will appear. More inflorescences appear a few weeks later so that a full flowering and salable plant can have 6 to 9 pinkinflorescences. Due to the long life of the inflorescences, green flowers are also visible on the plant. Smaller blossoms may occur on less mature growth. The lastingness of the inflorescence is 20 weeks in winter and 30 weeks in summer.

Reproductive organs:

*Size.*—The spadix measures approximately 2.5 to 5.5 cm in height. The length of the spadix is smaller than the length of the spathe. The spadix is columnar in shape. The width of a mature spadix that is approximately 5.5 cm long is approximately 11 mm to 12 mm at the base and approximately 8 mm to 9 mm at the top. The spadix angle with the spathe is approximately 75 to 85 degrees. The flower diameter on the spadix is 2 mm; with approximately 180 flowers on a full grown spadix of 5.5 cm long.

*Color.*—At the time the spathe unrolls, the spadix is unripe. The color of the spadix is light green (RHS 145A) at the tip and pale green (RHS 145C) at the base. As the spadix matures, it becomes first fully white (RHS 157C) and then turns slightly towards green (RHS 143B). When the pistil has been pollinated, there will exist berries on the spadix. The number of berries after pollination range from 1 up to 180. The size of the berries is 0.1 cm just after pollination, to 0.4 cm after approximately 26 weeks. The color of the berries ranges from green (RHS 137B) for unripe berries, to brown-yellow (RHS 169B to 169C) for ripe berries.

*Stamens.*—Anthers and filaments are not clearly visible on the spadix.

*Pollen.*—Minimal, white in color.

*Pistil.*—Light green (RHS 145A) at the tip and pale green (RHS 145C) at the base. The pistil protrudes from the spadix.

Roots: Grey-white roots with smaller hairy laterals. The root-tips are yellow.

Disease/pest resistance: No known resistance and/or susceptibility to diseases and pests.

I claim:

1. A new and distinct *Anthurium andreanum* plant named 'Anthefaqyr', as herein described and illustrated.

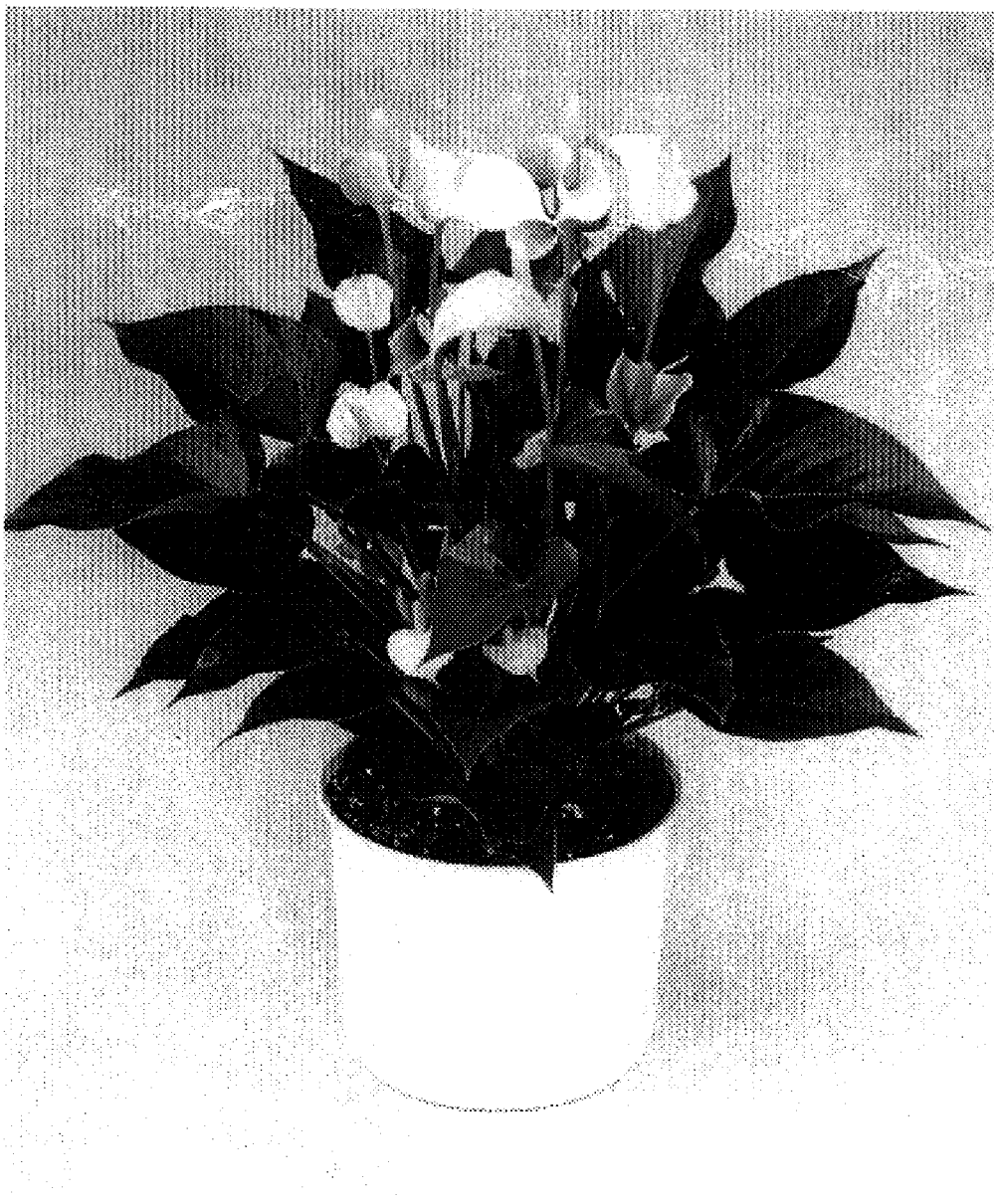

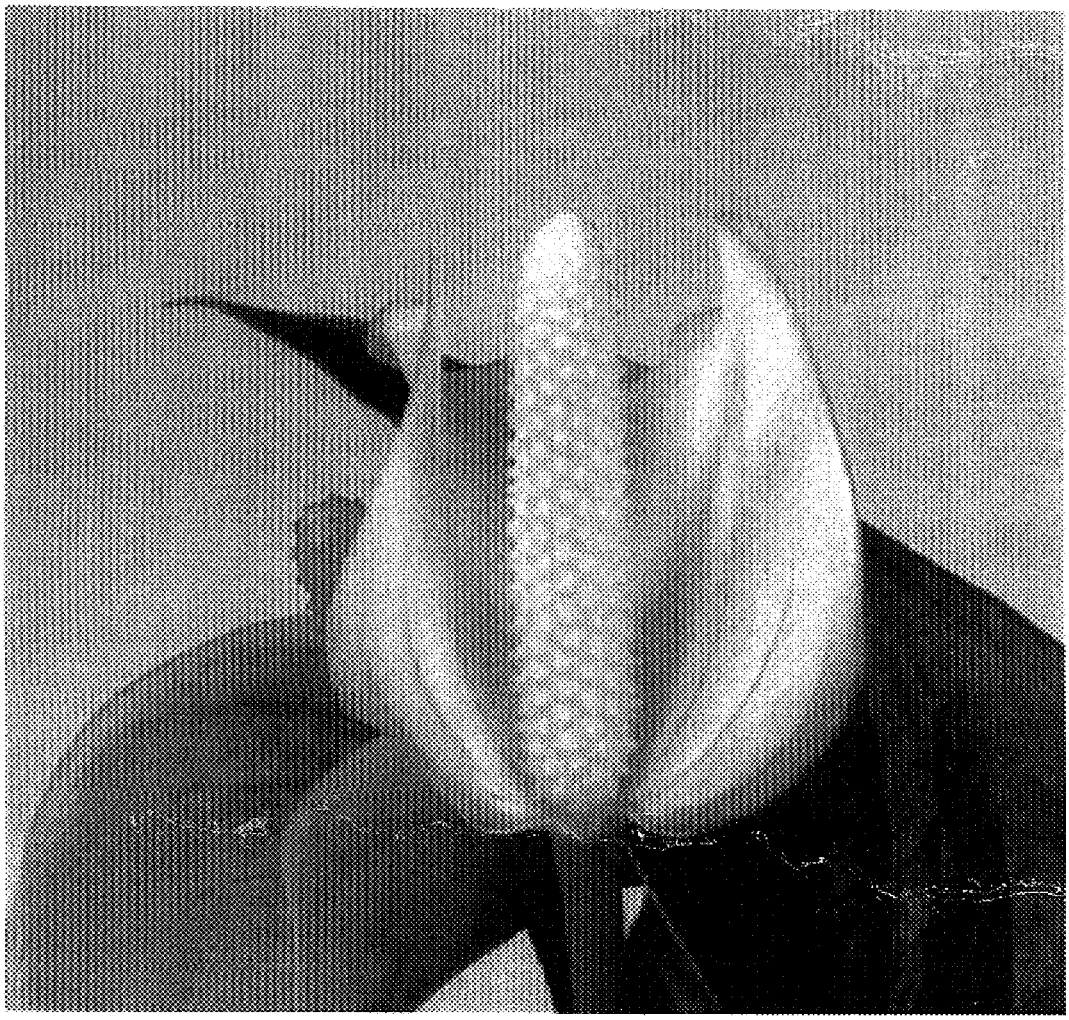

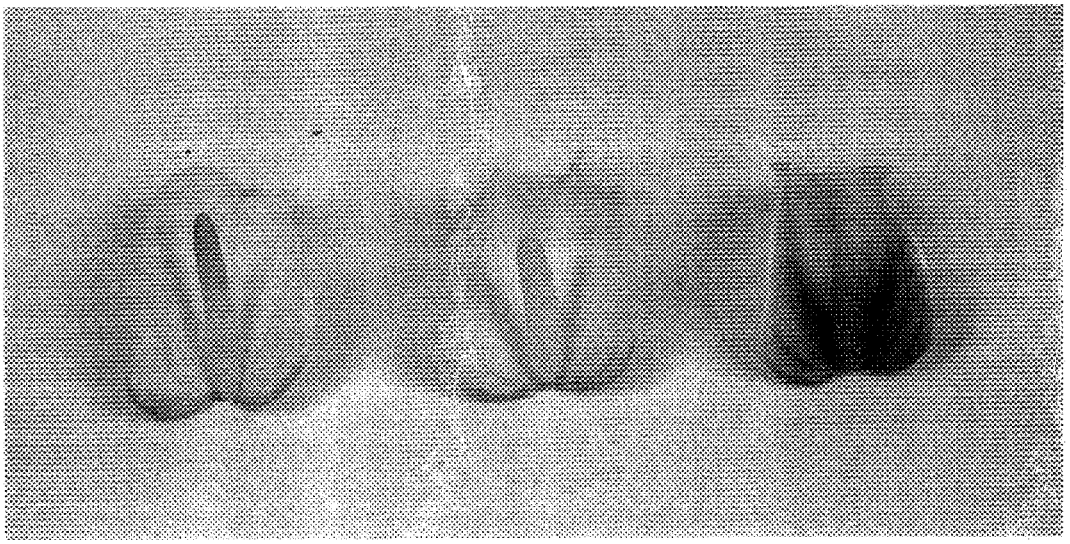

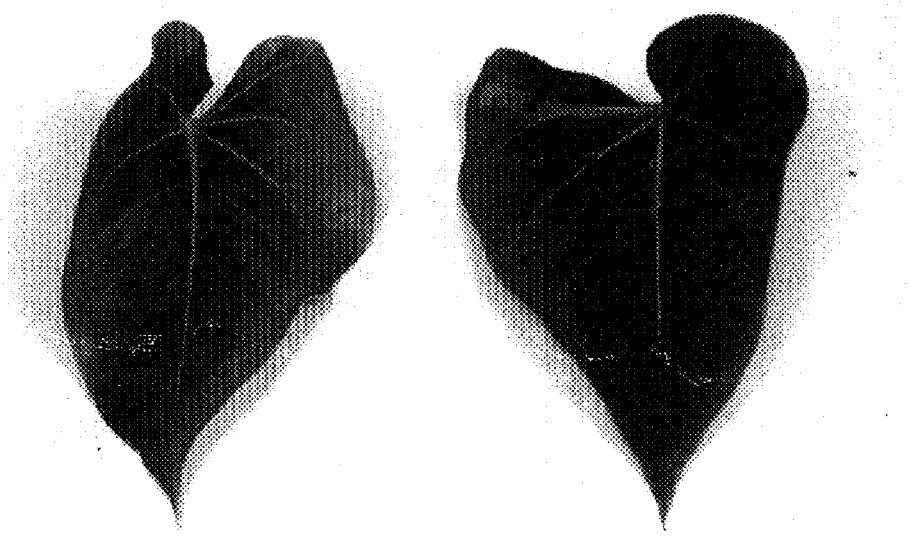

* * * * *